United States Patent [19]

Goodrich

[11] 4,282,121

[45] Aug. 4, 1981

[54] RESILIENT STARCH GRAFT POLYMER POLYHYDRIC ALCOHOL PRODUCT

[75] Inventor: Phillip W. Goodrich, St. Paul, Minn.

[73] Assignee: Henkel Corporation, Minneapolis, Minn.

[21] Appl. No.: 83,128

[22] Filed: Oct. 9, 1979

[51] Int. Cl.³ .............................................. C08L 3/02
[52] U.S. Cl. ..................... 260/17.4 GC; 260/17.45 G
[58] Field of Search ................................ 260/17.4 GC

[56] References Cited

U.S. PATENT DOCUMENTS

| | | | |
|---|---|---|---|
| 4,072,640 | 2/1978 | Sosa | 260/17.4 GC |
| 4,172,058 | 10/1979 | Hall | 260/17.4 GC |

*Primary Examiner*—Edward M. Woodberry
*Attorney, Agent, or Firm*—Patrick J. Span

[57] ABSTRACT

A starch-hydrolyzed polyacrylonitrile graft copolymer dispersed in polyhydric alcohols such as glycerol combines to form a resilient, soft, shock absorbent type material after heating. The material is useful for seat pads, artificial limb pads, toys and other applications where resilient, soft, shock absorbent materials find utility.

4 Claims, No Drawings

RESILIENT STARCH GRAFT POLYMER POLYHYDRIC ALCOHOL PRODUCT

This invention relates to a resilient starch graft polymer-polyhydric alcohol product. A resilient, soft, shock absorbent type material is formed by heating a mixture of a starch-hydrolyzed polyacrylonitrile copolymer dispersed in a polyhydric alcohol such as glycerol. The material is useful for seat pads, artificial limb pads, toys and other applications where resilient, soft, shock absorbent or foam like type materials find utility.

BACKGROUND OF THE INVENTION

Starch-hydrolyzed polyacrylonitrile graft copolymers exhibiting the capacity to absorb from about 300 to 1000 times their weight of deionized water are known at this time. The development of these compositions was carried out by the Northern Regional Research Laboratory, Peoria, Illinois. The starch-hydrolyzed polyacrylonitrile graft copolymer is produced by exposure of starch, either gelatinized or ungelatinized, to a catalyst such as ceric ammonium nitrate which acts as a catalyst to generate free radicals in the starch chain. Polyacrylonitrile chains become attached to these free radicals by copolymerization. A wide range of substitution in these copolymers is known in the art. For example, U.S. Pat. No. 3,935,099 and the divisional applications thereof, now U.S. Pat. Nos. 3,981,100, 3,985,616, and 3,997,484, show the preparation of copolymers in which the starch to polyacrylonitriles molar ratios range from 1:1.5 to 1:9. The variations in molar ratio of the components of the copolymer is not critical to the practice of this invention. The resulting material is then saponified in sodium hydroxide to hydrolyze the polyacrylonitrile chains to carboxy amide and alkali metal carboxylate groups mixed with metal salts. Drying the hydrolyzed material can be accomplished by tumble air drying or vacuum drying. After drying, the material can absorb about 300 to 400 times its weight. Washing the copolymer before drying with alcohol increases its absorbency to 800 to 1000 times its weight.

These copolymers are now commercially available one of these being sold under the trademark SGP by Henkel Corporation. In addition, the product is sometimes referred to as "Super Slurper". The copolymer can be made as film, flakes, powder or mat. These forms take up water, swelling but not dissolving and hold it in expanded duplications of their own dry shapes. Films extend and thicken in all dimensions. Powders become piles of water textured like crushed ice. A flake expands to a clear, angular piece of water. The swollen forms shrink in dilute acid, expand again in dilute alkali solution. They also shrink as they dry and expand again when absorbing water.

The copolymer, with these properties, can be mixed with or coated on a wide variety of materials including, for example, sand, straw, sawdust, seeds and roots, natural or synthetic fibers, flour, gelatin, and starch. It can hold water in soils, animal bedding and kitty litter, toweling and diapers, bandages, surgical pads, and dental absorbents.

SUMMARY OF THE INVENTION

It has now been discovered that starch-hydrolyzed polyacrylonitrile graft copolymer when dispersed in a polyhydric alcohol, such as glycerol, combines to form a resilient, soft, shock absorbent type material after heating. The product contains about 5% to 60% by weight of the starch graft copolymer and about 95% to 40% by weight of the polyhydric alcohol based on the total weight of graft copolymer and polyhydric alchol.

DETAILED DESCRIPTION AND PREFERRED EMBODIMENTS

The starch-hydrolyzed polyacrylonitrile graft copolymers are well known and commercially available as indicated in the "Background of the Invention" above. In the examples to follow the product employed was the commercially available product SGP 502S which is typically a dry powder having a moisture content in the range of about 3-6% by weight, a methanol content of about 1% by weight and a fluid absorbency of a 1% saline solution of about 80-90%. The powder is available in varying granulations, the granulation of the material used in the examples to following being a −100 mesh.

The commercial product may also be described generally as a polymer composed of a naturally occurring polymer (starch) and a synthetic polymer (acrylamide and alkali metal acrylate). Proportions of starch and acrylic polymer are about 2:3 while the proportion of acrylate and acrylamide are about 3:1.

The polyhydric alcohols employed are those commonly referred to as the sugar alcohols which bear a close relationship to the simple sugars from which they are formed and from which their names are often derived. These polyols contain straight carbon chains in which each carbon atom bears a hydroxyl group. The sugar alcohols may also be defined by the general formula:

$$HOCH_2(CHOH)_nCH_2OH \text{ where } n \text{ is } 2\text{-}5.$$

Among these alcohols are glycerol, erythritol, xylitol, sorbitol, mannitol and dulcitol with glycerol, erythritol, xylitol and sorbitol being most preferred or desirable for the purposes of this invention.

Based on the total weight of the starch graft copolymer and the sugar alcohol, the product will be prepared generally using about 5-60% of the starch graft copolymer and about 95-40% of the polyhydric alcohol. This will depend somewhat on the particular sugar alcohol employed. More desirably about 10 to 40% starch graft copolymer and 90 to 60% sugar alcohol is employed with the preferred amounts being about 20% starch graft polymer and 80% sugar alcohol.

The product is prepared by dispersing the starch graft polymer in a sugar alcohol, such as glycerol, in the desired weight ratio and heating above room temperature (about 23° C.) up to temperatures of 120° C. A soft, resilient, though sometimes sticky, material results after heating which is useful for seat pads, artificial limb pads, toys and other applications where resilient, soft, shock absorbent or foam-like materials find utility.

In the following examples, all parts and percentages are by weight unless otherwise indicated.

EXAMPLE I

Eighty (80) grams of glycerol was weighed into a 150 ml. beaker to which was added 20 grams of a starch-hydrolyzed polyacrylonitrile graft copolymer (SGP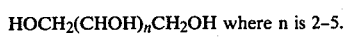 502S). The copolymer and glycerol was stirred with a glass mixing rod and the mixture placed in a forced air oven set at 80° C. overnight. Upon initial mixing the mixture took on a greenish tint. After heating the mixture was a tough, rubbery, sticky mass.

EXAMPLE II

In this example mixtures of varying amounts of the starch graft copolymer and glycerol were studied. Mixtures were prepared in beakers using a stirring rod as follows:

| Sample | Starch Copolymer (grams) | Glycerin (grams) |
|---|---|---|
| 1 | 20 | 180 |
| 2 | 40 | 160 |
| 3 | 60 | 140 |
| 4 | 80 | 120 |
| 5 | 50 | 50 |
| 6 | 30 | 20 |
| 7 | 40 | 10 |

All of the mixtures were heated to 90° C. for 2 hours and allowed to cool to room temperature. Sample 1 settled out before it could set. The material in the bottom of the beaker had the soft, resilient sticky characteristics. Samples 2, 3 and 4 were sticky, rubbery mats, sample 2 being the softest, stickiest and most resilient. Sample 4 was hard and barely sticky. Sample 5 was a chunk of consolidated granules which could be broken up into sticky granules. Samples 6 and 7 were granular materials which tend to stick together and not flow. When placed in water it does not block but absorbs slowly.

EXAMPLE III

One hundred (100) grams of starch graft copolymer were added to 400 grams of glycerol in a 1 quart blender cup. To this was added 5 grams of paraformaldehyde (5% based on the starch copolymer.) Agitation was continued until all ingredients were thoroughly mixed. The mixture was poured into a dish coated with a mold release agent and placed in a forced air oven at 80° C. for 2 hours. The product had the same properties as that of Example I i.e. sticky and rubbery with slow hydration in water.

The foregoing was repeated using 25 grams of paraformaldehyde. After 2 hours at 80° C. the product was rubbery but had much less stretch and snapped if pulled too far. The product was placed in an oven at 110° C. for 2 hours after which the oven was turned off and the product left overnight. The next morning the product was a dense, smelly foam which has expanded in every dimension by an estimated 10–20%. When placed in water it absorbed without swelling and produced a transparent, colorless, brittle gel.

The embodiments of the invention in which an exclusive property or privilege is claimed are defined as follows:

1. A composition comprising the reaction product at temperatures of about 23° C. to 120° C. of a starch-hydrolyzed polyacrylonitrile graft copolymer and a sugar alcohol having the general formula $HOCH_2(CHOH)_nCH_2OH$ where n is 2–5 and wherein, based on the total weight of starch graft polymer and sugar alcohol, said starch graft polymer is present in an amount of about 5–60% by weight and said sugar alcohol is present in an amount of about 95–40% by weight.

2. A composition as defined in claim 1 in which said starch graft polymer is present in an amount of about 20%.

3. A composition as defined in claim 1 in which said sugar alcohol is selected from the group consisting of glycerol, erythritol, xylitol, sorbitol and mannitol.

4. A composition as defined in claim 1 in which said sugar alcohol is glycerol.

* * * * *